United States Patent [19]

Prochazka et al.

[11] Patent Number: 5,562,707
[45] Date of Patent: Oct. 8, 1996

[54] GARMENT FOR APPLYING CONTROLLED ELECTRICAL STIMULATION TO RESTORE MOTOR FUNCTION

[75] Inventors: Arthur Prochazka; Marguerite Wieler; Zoltan R. Kenwell; Michel J. A. Gauthier, all of Edmonton, Canada

[73] Assignee: Sim & McBurney, Toronto, Canada

[21] Appl. No.: 408,828

[22] Filed: Mar. 22, 1995

[30] Foreign Application Priority Data

Oct. 13, 1993 [GB] United Kingdom ............... 9321086
Oct. 13, 1994 [WO] WIPO ................. PCT/CA94/00570

[51] Int. Cl.$^6$ .................................................. A61N 1/36
[52] U.S. Cl. ............................................ 607/2; 607/48
[58] Field of Search .................... 607/2, 145, 146, 607/150, 152, 111, 102, 115

[56] References Cited

U.S. PATENT DOCUMENTS

| | | | |
|---|---|---|---|
| 3,610,250 | 10/1971 | Sarbacher | 128/379 |
| 4,391,279 | 7/1983 | Stein | 128/643 |
| 4,558,704 | 12/1985 | Petrofsky | 128/423 |
| 4,569,352 | 2/1986 | Petrofsky et al. | 607/49 |
| 4,580,572 | 4/1986 | Granek et al. | 128/639 |
| 4,583,547 | 4/1986 | Granek et al. | 128/639 |
| 4,763,660 | 8/1988 | Kroll et al. | 128/640 |
| 4,785,813 | 11/1988 | Petrofsky | 128/421 |
| 4,911,169 | 3/1990 | Ferrari | 128/641 |
| 5,121,747 | 6/1992 | Andrews | 128/423 |
| 5,193,540 | 3/1993 | Schulman et al. | 128/419 R |
| 5,330,516 | 7/1994 | Nathan | 607/48 |

FOREIGN PATENT DOCUMENTS

| | | | |
|---|---|---|---|
| 2064151 | 9/1992 | Canada | A61N 1/08 |
| 0435416 | 6/1990 | European Pat. Off. | A61N 1/04 |
| 2186191 | 8/1987 | United Kingdom | A61N 1/36 |

OTHER PUBLICATIONS

The Journal of Physiology, edited for the Physiological Society, by W. Almers et al., vol. 343, 1983: Caambridge University Press, pp. 20p–21p.

Treatment of the Hemiplegic Upper Extremity Using Electrical Stimulation and Biofeedback Training, by R. Waters, M.D. et al., Report to the Veterans Administration Sep. 1980; pp. 253–266.

Functional Neuralmuscular Stimulation for Restoration of Hand Grasp, by P. E. Crago, Ph.D. et al., from the Applied Neural Control Laboratory Biomedical Engineering Department, Case Western Reserve Univ., Sep. 1991; pp. 20–23.

FES–Control of Multijoint System in the Paralyzed Upper Limb, Osaka International Workshop on FNS, Nov. 1989; pp. 91–95.

Primary Examiner—William E. Kamm
Assistant Examiner—Scott M. Getzow
Attorney, Agent, or Firm—Benman Collins & Sawyer

[57] ABSTRACT

A non-invasive self-contained functional electrical stimulation garment is disclosed. The garment, which is preferably in the form of a glove, may be donned in one piece by a user of reduced motor ability e.g. a person exhibiting hand tremors or who is a quadriplegic, paraplegic or hemiplegic. The garment is preferably made of a perforated elastic material and being adapted to fit over a part of said user's body. The garment has electrical connections internal to the garment that are adapted to make electrical contact with self-adhesive skin electrodes on the user. A joint movement sensor and a battery-driven electronic controller-stimulator located on the garment, with the electrical connections, sensor and controller-stimulator being electrically and cooperatively interconnected. In the form of a glove, the garment can permit a user of reduced motor ability to grip objects.

29 Claims, 10 Drawing Sheets

GARMENT FOR APPLYING CONTROLLED ELECTRICAL STIMULATION TO RESTORE MOTOR FUNCTION

FIELD OF THE INVENTION

This invention relates to apparatus for stimulating muscles in the human body, especially a garment for applying controlled electrical stimulation to restore motor function and a device for stimulating muscles used to provide pinch grip and hand opening functions. The device is intended for use by partially paralyzed people or people with hand or other tremor.

BACKGROUND OF THE INVENTION

The use of signals from switches or sensors to control functional electrical stimulation (FES) of paralyzed muscles is known. Use of a shoulder position sensor to control wrist extension via an implanted FES stimulator has been described (Vodovnik, L. (1971) Development of Orthotic Systems using functional electrical stimulation and myoelectric control, Progress Report, University of Ljubljana, prepared for U.S. Dept. of Health Education and Welfare Social and Rehabilitation Service, under contract No. SRS-YUGO 23-68). Shoulder sensors have also been used to control hand opening and pinch-grip (Peckham, P. H., Marsolais, E. B. & Mortimer, J. T. (1980) J. Hand Surgery, 5,462–469; Peckham, P. H. & Keith, M. W. (1992) "Motor prostheses for restoration of upper extremity function" In: Neural Prostheses: Replacing Motor Function After Disease or Disability eds.: Stein, R. B., Peckham, P. H. & Popovic, D. B. New York: Oxford University Press; EP-145504-A, U.S. Pat. No. 4,558,704 and CA1263446-A, all of Wright State University. A wrist position sensor has been used to control FES of leg muscles (Prochazka, A. & Wiles, C. M. (1983) "Electrical stimulation of paretic leg muscles in man, allowing feedback-controlled movements to be generated from the wrist" J. Physiol. 343, 20P). A switch mounted on a watch band has been used to trigger FES—evoked pinch-grip (Handa, Y., Itchie, M., Handa, T., Takahashi, H. Saito, C., Kameyama, J. & Hoshimiya, N. (1989) "FES-control of multijoint system in the paralysed upper limb". Osaka Int. Workshop on FNS. pp. 91–95.). A multi-component device in which wrist position sensors are used to stimulate FES evoked pinch-grip has also been described (Crago, P. E., Peckham P. H., Mansour, J. M., Lan, N., Kilgore, K. and Chizeck, H. J. (1991) a, b, c,) "Functional neuromuscular stimulation for restoration of hand grasp" NIH Contract NO1-NS-9-2356 7th, 8th & 9th Progress Reports, June, September & December, 1991; Crago, P. E. Peckham, P. H. Mansour, J. M., Lan, N., Kilgore, K. and Chizeck, H. J. (1992). "Functional neuromuscular stimulation for restoration of hand grasp". NIH Contract NO1-NS-9-2356. 10th, 11th & 12th Progress Reports, March, June, September, 1992; Peckham, P. H. & Keith, M. W. (1992) "Motor prostheses for restoration of upper extremity function" In: Neural Prostheses: Replacing Motor Function After Disease or Disability, eds.: Stein, R. B., Peckham, P. H. & Popovic, D. B. New York: Oxford University Press). The use of FES to attenuate tremor was reported by Prochazka, A., Elek, J. and Javidan, M. (1992) "Attenuation of pathological tremors by functional electrical stimulatation" I. Technique, Annals of Biomedical Engineering, 20: 205–224.

Several of the approaches described above involve percutaneous wire electrodes, or fully implanted FES simulators i.e. invasive procedures are required to the hand and wrist in order to achieve a working system. Such previous systems also required extensive customization for each user using the systems and because they comprised several discrete components which required separate attachment to the patient, they were inconvenient to use. In none of the previous systems had a device been described which would permit movement-disabled persons to simply and independently don and remove a self-contained device for wrist-activated hand control.

SUMMARY OF THE INVENTION

According to a particular aspect of the present invention, a device in the form of a fingerless glove is provided which electronically senses voluntary wrist movements and provides controlled FES of muscles in the hand and forearm either to produce a pinch-grip or open the hand. The device enables a motor impaired person to use non-invasive surface FES for hand control in daily life, independently or with minimal help. It also provides a convenient means for therapeutic muscle stimulation. Conductive areas on the internal surface of the glove automatically make contact with self-adhesive electrodes previously placed on the skin over selected muscles. Trains of electrical pulses are delivered via these electrodes through the skin into the target muscles, causing them to contract. In the preferred embodiment, the source of the electrical stimuli is a battery-powered electronic circuit located in a flat box in a pocket on the back of the glove. Wrist movements are sensed by a displacement transducer which spans the wrist joint from the flat box to a point on the back of the hand portion of the glove.

Accordingly, one aspect of the present invention provides a non-invasive self-contained functional electrical stimulation garment which may be donned in one piece by a user of reduced motor ability, comprising:

said garment being made of an elastic material, preferably a perforated elastic material, and being adapted to fit over a part of said user's body;

electrical connections internal to said garment adapted to make electrical contact with self-adhesive skin electrodes on said user;

a joint movement sensor on said garment;

a battery-driven electronic controller-stimulator located on said garment; and said electrical connections, sensor and controller-stimulator being electrically and cooperatively interconnected.

In preferred embodiments, electrical contact is formed on tightening of the garment on the user, preferably through a metallic mesh or a metallic foil which is pressed down onto metallic studs on the electrodes.

The garment is preferably in the form of a hand glove, especially a glove that fits over at least part of a hand and part of the forearm of the user, with the sensor preferably being a wrist movement sensor. Other embodiments comprise a single sleeve or cuff which fits over one segment of a limb, with the sensor either extending from the sleeve or cuff, over an adjacent joint to a point of attachment on the skin, or a proximity detector which transduces relative motions of an adjacent limb segment such as the hand by monitoring changes in electric or magnetic fields, or changes in the intensity of sound or light transmitted from the adjacent limb segment or changes in the stretching of skin underlying the garment.

In preferred embodiments, the garment is capable of being tightened by the user e.g. using Velcro® straps and ring-pulls to enable a user of reduced motor ability to don and tighten the garment.

In other aspects, the present invention provides a non-invasive self-contained functional electrical stimulation hand glove which may be donned in one piece by a user of reduced motor ability, comprising:

said glove being made of an elastic material and being adapted to fit over a wrist on said user;

a wrist movement sensor on said glove; and a functional electrical controller-stimulator located on said glove, said sensor and said controller-stimulator being electrically and cooperatively interconnected.

In aspects of the invention, the closing and opening of the hand of the user is stimulated on movement of the wrist of the user beyond threshold limits of flexion and extension thereof, with an intermediate zone between such threshold limits in which there is no stimulation to open or grip, the threshold limits being set on said controller.

In other aspects, electrical contact is made with pre-positioned self-adhesive skin electrodes when glove is tightened.

Aspects of the invention additionally provide a non-invasive self-contained functional electrical stimulation hand glove which may be donned in one piece by a user of reduced motor ability, comprising:

a wrist movement sensor on said glove;

a functional electrical controller-stimulator located on said glove;

opening and closing with the hand being controlled by the controller-stimulator by movement of the wrist beyond threshold limits of flexion and extension thereof, with an intermediate zone between such threshold limits in which there is no stimulation to open or close.

Further aspects provide a non-invasive self-contained functional electrical stimulation garment which may be donned in one piece by a user of reduced motor ability, comprising:

said garment being made of an elastic material, preferably perforated elastic material, and being adapted to fit over a joint on said user;

metallic mesh patches internal to said garment adapted to make electrical contact with self-adhesive skin electrodes when garment is tightened by the user;

said self-adhesive skin electrodes including a stud oriented away from the skin of the user, said stud connecting to the metal mesh by contact pressure.

In aspects of the invention, the closing and opening of the hand of the user is stimulated on movement of the wrist of the user beyond threshold limits of flexion and extension thereof, with an intermediate zone between such threshold limits in which there is no stimulation to open or grip, the threshold limits being set on said controller. In another aspect of the invention, the mode of stimulation is for therapeutic, muscle-strengthening purposes in people with hemiplegia due to stroke or trauma. In this aspect, after donning the garment, one of several pre-stored programs of cyclical stimulation is selected by the user. The sensor in this embodiment is used to set stimulus strengths and other parameters of the cyclical program.

In other aspects, electrical contact is made with pre-positioned self-adhesive skin electrodes when glove is tightened.

The present invention also provides a method of effecting muscle stimulation of a user of reduced motor ability, comprising:

determining selected muscle stimulation sites on said user;

applying self-adhesive skin electrodes at said sites; and applying a garment as disclosed herein.

The garment or glove may be used by users with quadriplegia, paraplegia or hemiplegia or by users with tremor.

A detailed description of the preferred embodiment is provided herein below with reference to the following drawings, in which:

DETAILED DESCRIPTION OF THE INVENTION

The present invention will be particularly described herein with reference to a glove and a wrist movement sensor. However, it is to be understood that the invention may be in the form of another garment that fits over a joint of a user and that the sensor relates to movement of that joint e.g. ankle, elbow or the like.

Figure 1:
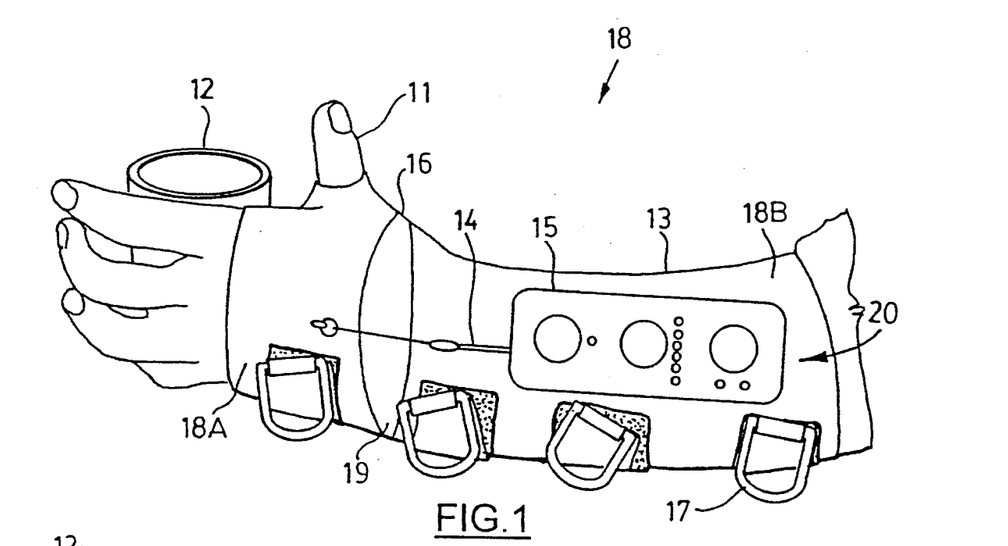
FIG. 1 is a perspective view of the device according to the preferred embodiment, shown with a patient's hand in the device in the open position.

Turning to the figures, a device for controlled pinch-grip and hand opening is illustrated in FIG. 1. In FIG. 1, a hand 11 is shown in an open position around a drinking glass 12. As can be seen from FIG. 1, the stimulator device, generally indicated by 18, takes the form of a fingerless glove 13 worn on the hand and forearm. In the preferred embodiments, glove 13 is made principally of the elastic material neoprene, punched with small holes for breathability. Lycra® mesh 16 links the hand and forearm portions (18A and 18B, respectively) of glove 13 over the wrist crease 19. Horse-hide, deer-hide or rubber are preferred materials for forming the palm section of hand portion 18A of stimulator device 18, to maximize traction on wheel-chair rims i.e. when the user moves a wheelchair in which he/she is seated. Wrist position sensor 14 is illustrated with the proximal end of the sensor located in long, flat control box 15 which is held in a pouch generally indicated by 20 on the back of glove 13; although not shown, pouch 20 may be formed of a netting or other suitable material to hold box 15 in place, while permitting access to its functions as disclosed herein. Glove 13 has D-rings 17 which are attached to Velcro® straps (shown as 50 in FIG. 5). D-rings 17 are used to close and tighten each strap in turn. Preferably, D-rings 17 are of a large size to enable a patient to insert a finger into a ring to pull a strap tight.

Figure 2:
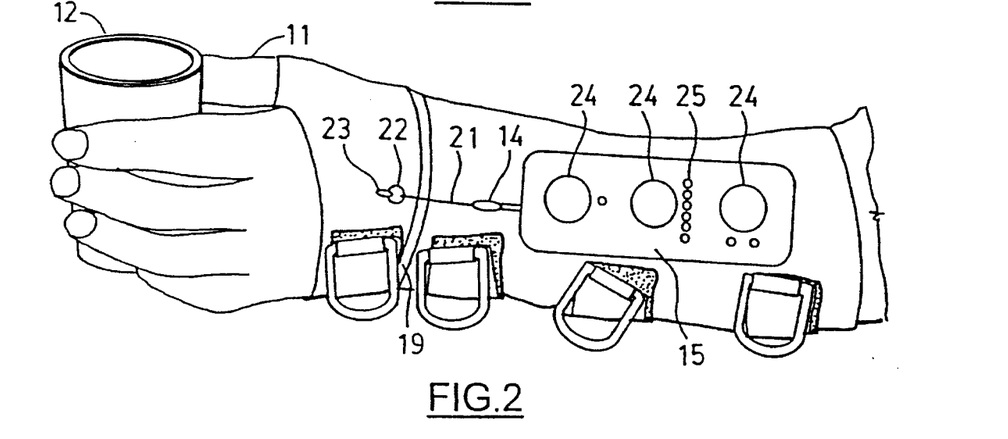
FIG. 2 is a perspective view of the device shown in FIG. 1, having the patient's hand in a closed position.
Figure 5:
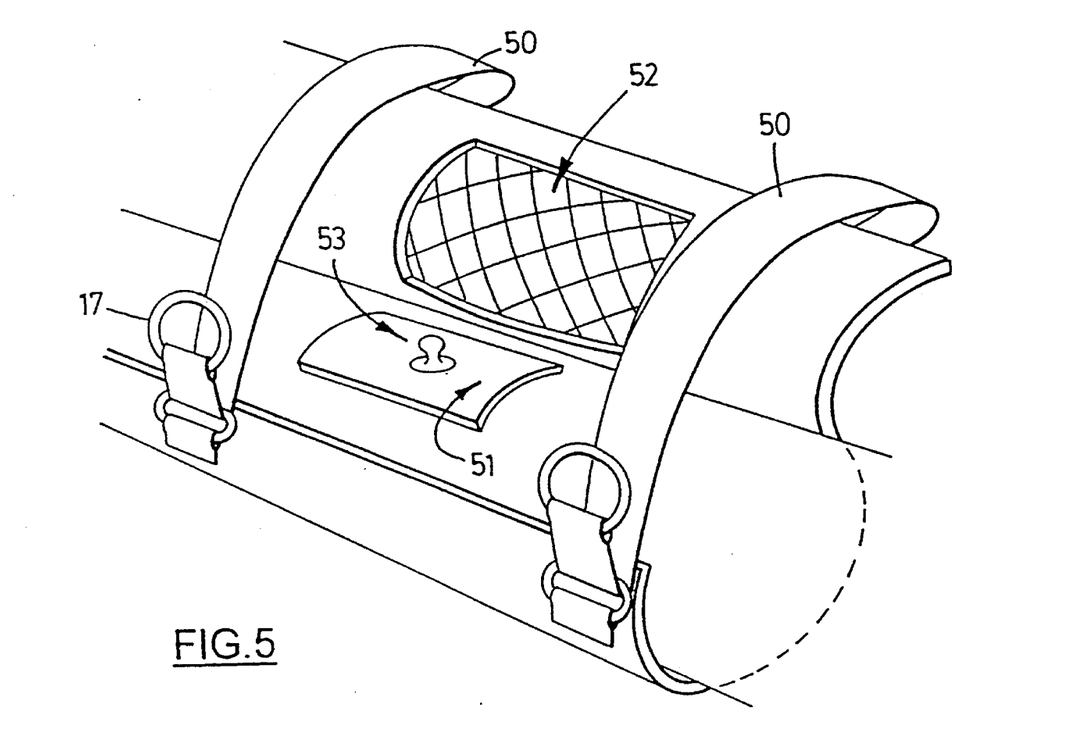
FIG. 5 is a perspective view of the conductive electrodes and metal-mesh connector pad of the device of FIG. 1.

In FIG. 2, glove 13 of FIG. 1 is shown with hand 11 and glass 12. In FIG. 2, the user's hand 11 is shown in a pinch-grip position. Sensor 14 is spring-loaded, and is pulled out of box 15 by durable thread 21 which traverses wrist joint crease 19 and ends in ring 22 attached to hook 23 sewn to the back of wrist portion 18A of glove 13. Large buttons 24 flush with the surface of control box 15 allow the patient to control several stimulus parameters. Light-emitting-diodes (LED) 25 show the user the options chosen by pressing buttons 24. Other means such as liquid crystal display or auditory speaker could show the user the options.

Figure 3:
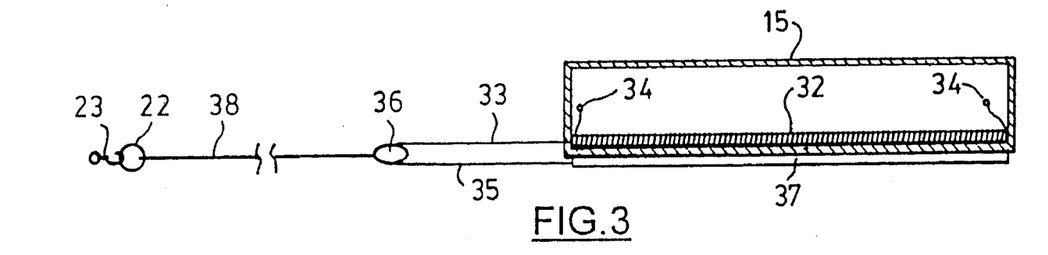
FIG. 3 is a cross-sectional view of the joint position sensor of the device of FIG. 1.

FIG. 3 shows a cross-section of wrist position sensor 14 of the preferred embodiment of the invention. Wrist-position sensor 14 is an inductive transducer e.g. a linear variable displacement transducer. Glass tube 32 of wrist position sensor 14 is located inside control box 15. A thin metal stylus 33 moves in and out of glass tube 32, changing the inductance of wire coil 34 wound onto tube 32. The stylus 33 and an elastic cord 35 are attached to a smooth glass bead 36. Plastic tube 37 of wrist sensor 14 is attached to the bottom surface of control box 15. Elastic cord 35 is held in tension in plastic tube 37 and pulls on bead 36 and therefore pulls the stylus 33 back into tube 32 i.e. plastic tube 37 and elastic cord 35 provide spring-loading of the stylus 33. A durable thread 38 leads from bead 36 over the back of the wrist to ring 22 which attaches to hook 23 sewn to the back of the hand portion 18A of glove 18. When the wrist is flexed, this pulls stylus 33 out of tube 32. The reduced inductance of coil 34 which this causes is decoded by electronic circuitry within box 15, providing the desire position signal. When the wrist extends, the spring-loading mechanism described above pulls stylus 33 back into tube 32, increasing the inductance of coil 34.

Figure 4:
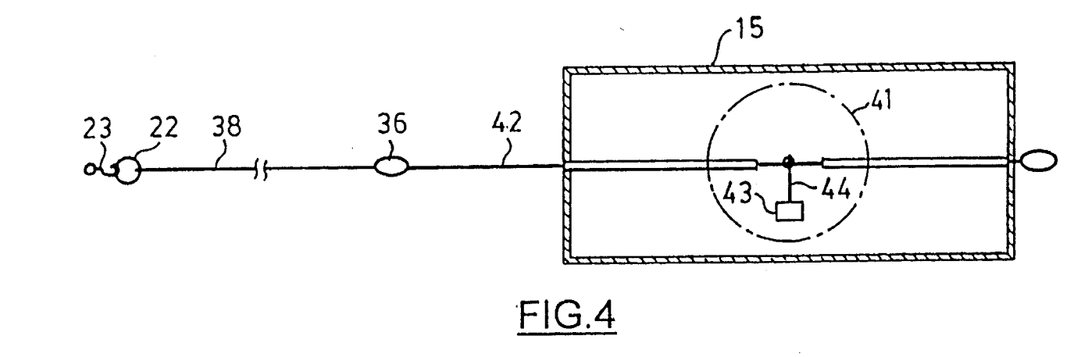
FIGS. 4, 4A and 4B are cross-sectional view and partial sectional views of alternative forms of the joint position sensor of FIG. 3.
Figure 4A:
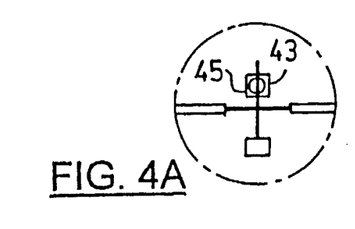
Figure 4B:
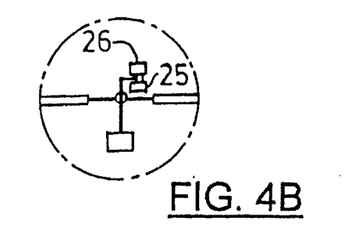

In FIG. 4, an alternative to wrist position sensor 14 of FIG. 3 is shown, in cross-sectional view. Housing 41 of wrist position sensor 14 is contained in box 15 on glove 13, while ring 22 is attached to hook 23 on the back of the hand portion 18A of glove 18. A compliant elastic cord or spring 42 in sensor 14 leads to glass bead 36. A durable thread 38 spans the wrist joint 19. A protective plastic sleeve covers part of the length of cord or spring 42 from box 15 to the wrist joint. The compliant cord or spring 42 is attached within the housing 41 of box 15 to a cantilever element 43, which has semiconductor strain gauges 44 bonded to it. When the wrist flexes, durable thread 38 extends compliant spring 42, and imparts increased force to the cantilever, bending it and changing the electrical resistance of the strain gauges. Two alternate sensing elements are shown in FIG. 4A and FIG. 4B. In FIG. 4A, the bending of cantilever element 43 is detected by a Hall-effect magnetic transducer 45. In FIG. 4B, the bending of cantilever element 43 is detected by a photoelectric sensor made up of a photoemitter such as a LED 25 and a photodetector such as a photodiode 26. The beam transmitted from LED 25 to photodiode 26 is partially blocked by a sidearm of cantilever 43, the amount being blocked depending on the position of cantilever element 43, which in turn depends on the tension in spring 42 and therefore the position of the wrist.

In an alternative to the embodiment of FIG. 4, which is not shown, wrist position sensor 14 is of the proximity-detector type. This could either detect changes in electric or magnetic fields caused by the proximity of the adjacent limb segment, or changes in the intensity of sound or light transmitted from or reflected by the adjacent limb segment, or changes in the stretching of skin underlying part of the garment.

FIG. 5 shows adhesive FES electrode 51 and stainless mesh contact pad 52 sewn between the inner surface of the gloves and an inner lining; straps 50 are shown in a loosened condition with forearm portion 18B of glove 13 in a partially opened position. An example of electrode 51 is a commercially available gel electrode exemplified by Conmed Corporation of Utica, N.Y., Type 650-2578. A metal stud 53 is located on the back of electrode 51, normally intended to connect to the clasp of a snap or press-stud connecter, may be augmented in height slightly with a small metal dome. The electrode thus modified is pressed onto the skin over the muscle to the stimulated. When glove 13 is donned, the corresponding metal mesh contact pad 52 presses onto stud 53 on the back of electrode 51, the contact pad is connected to the circuitry in box 15 by insulated stainless steel wire which leads from the pad to a connector on box 15. Donning the glove therefore automatically connects the skin through the electrode, the contact pad, the wire and the connector to the circuitry in box 15.

Figure 6:
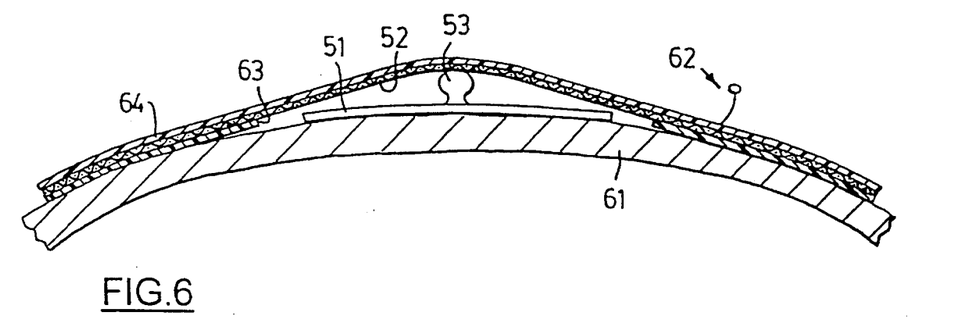
FIG. 6 is a cross-sectional view of the conductive electrodes and metal-mesh connector pad of the device of FIG. 1.

In FIG. 6, electrode 51 and contact pad 52 are shown in cross-section with electrode 51 mounted on the user's skin 61. The electrode's stud or dome 53 is shown in contact with the metal mesh pad 52. An electrical current is transmitted by way of insulated stainless steel wire 62, metal mesh contact pad 52 and stud 53 through electrode 51 into the user's skin 6 I; a solid conductive gel is usually located in electrode 51. Dome 53 must have sufficient height to press up firmly against the mesh pad 52 through an opening cut into the neoprene inner lining 63 inside the outer neoprene shell 64 of the glove. This ensures that no part of the metal mesh 52 contacts skin 61 directly.

Figure 7:
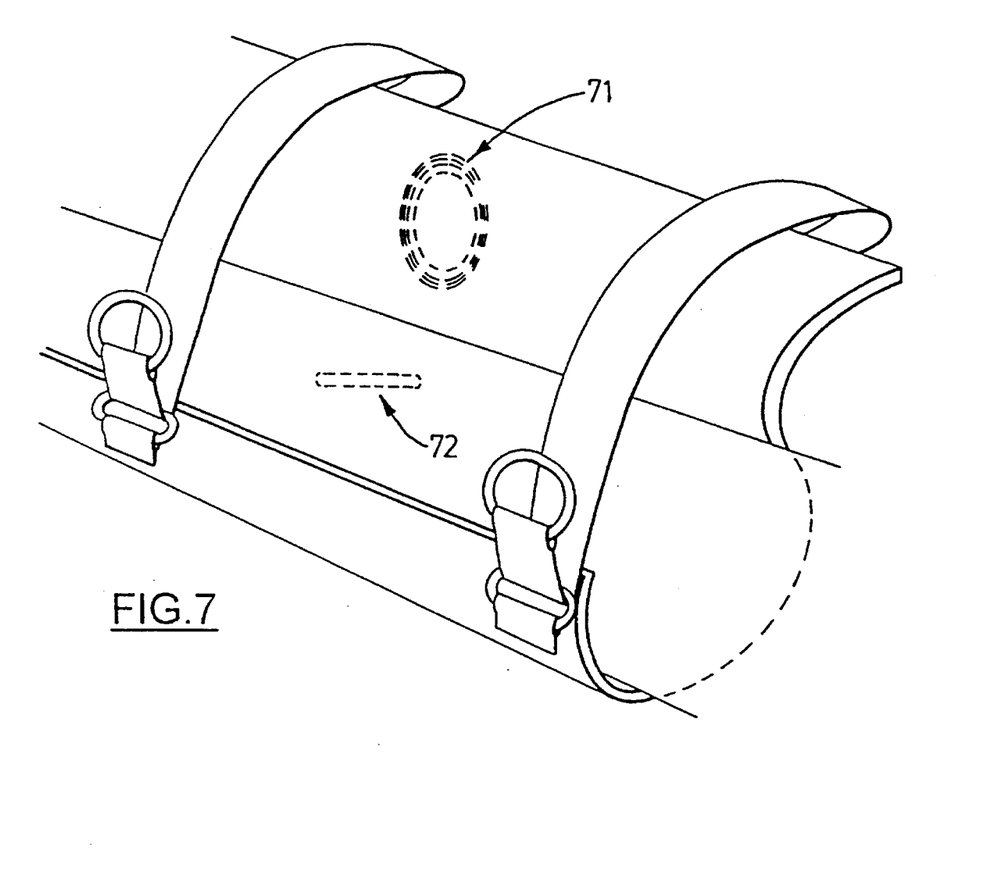
FIG. 7 shows an implanted alternative to the surface electrode system shown in FIG. 5 or 6.

FIG. 7 illustrates an implanted, and less preferred, alternative to the surface electrode system shown in FIG. 6. In this embodiment, the contact pad 52 is replaced by an antenna 71, which transmits electrical energy and commands from box 15 through the skin at radio frequencies, to an implanted muscle microstimulator 72. The micro stimulator and an external antenna might be in the form of the devices described by Schulman et al. U.S. Pat. No. 5,193,540.

Figure 8:
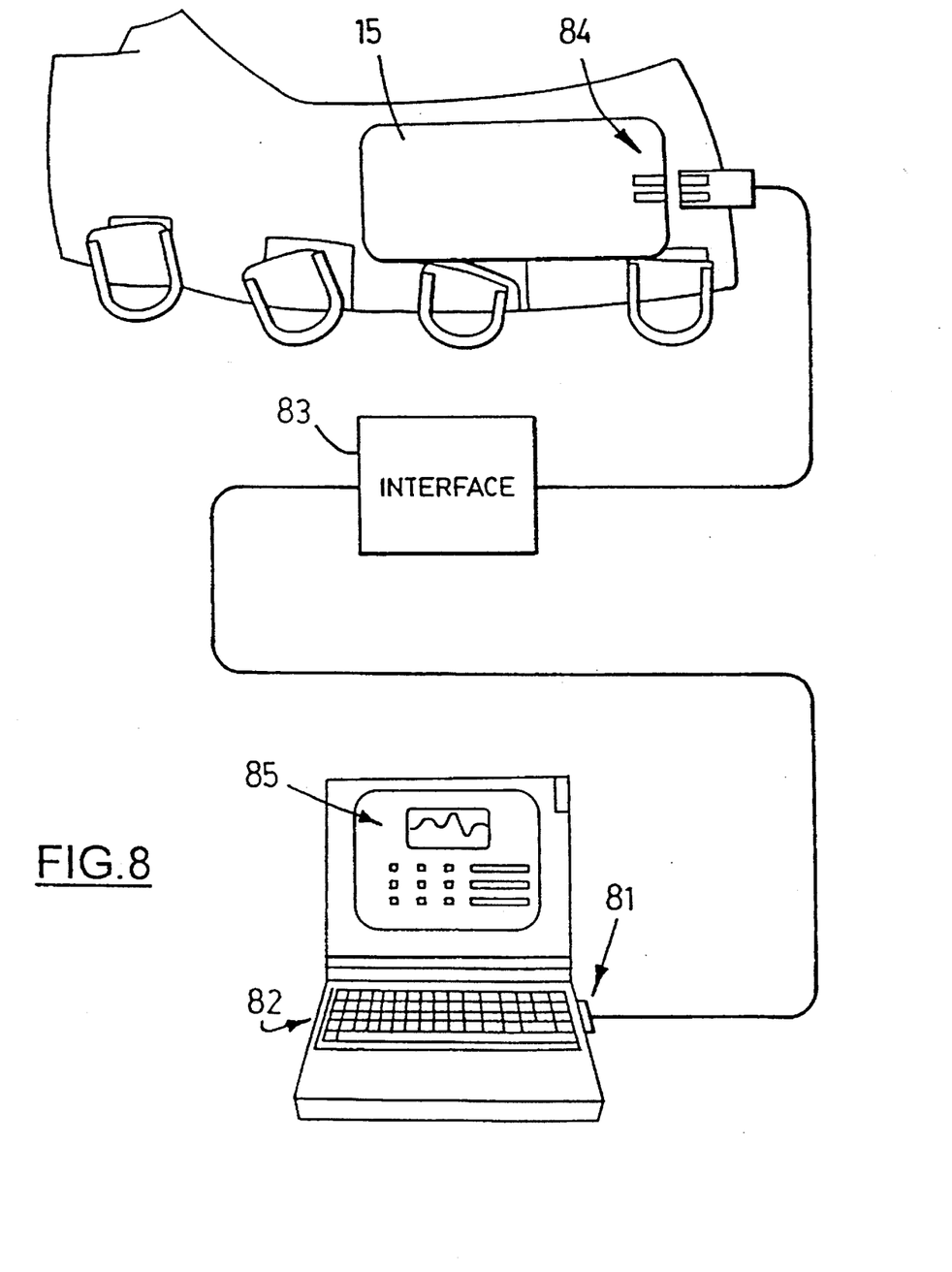
FIG. 8 illustrates the computer system and optical communication link which allows a clinician to re-set functional parameters of the device shown in FIG. 1.

FIG. 8 shows a computer system which allows a clinician to set functional parameters of glove 13 to suit a particular user. An RS232 communication port 81 of a personal or lap top computer 82 is connected by interface 83 to optical receive/transmit port 84 in box 15. A graphics-based display 85 of the computer allows parameters such as channel allocation, pulse train profiles and sensor hysteresis (see below) to be set easily. A microcontroller in box 15 sends prevailing parameter settings and the wrist position signal back to the computer, allowing sensor operation to be verified and parameters to be checked.

Figure 9:
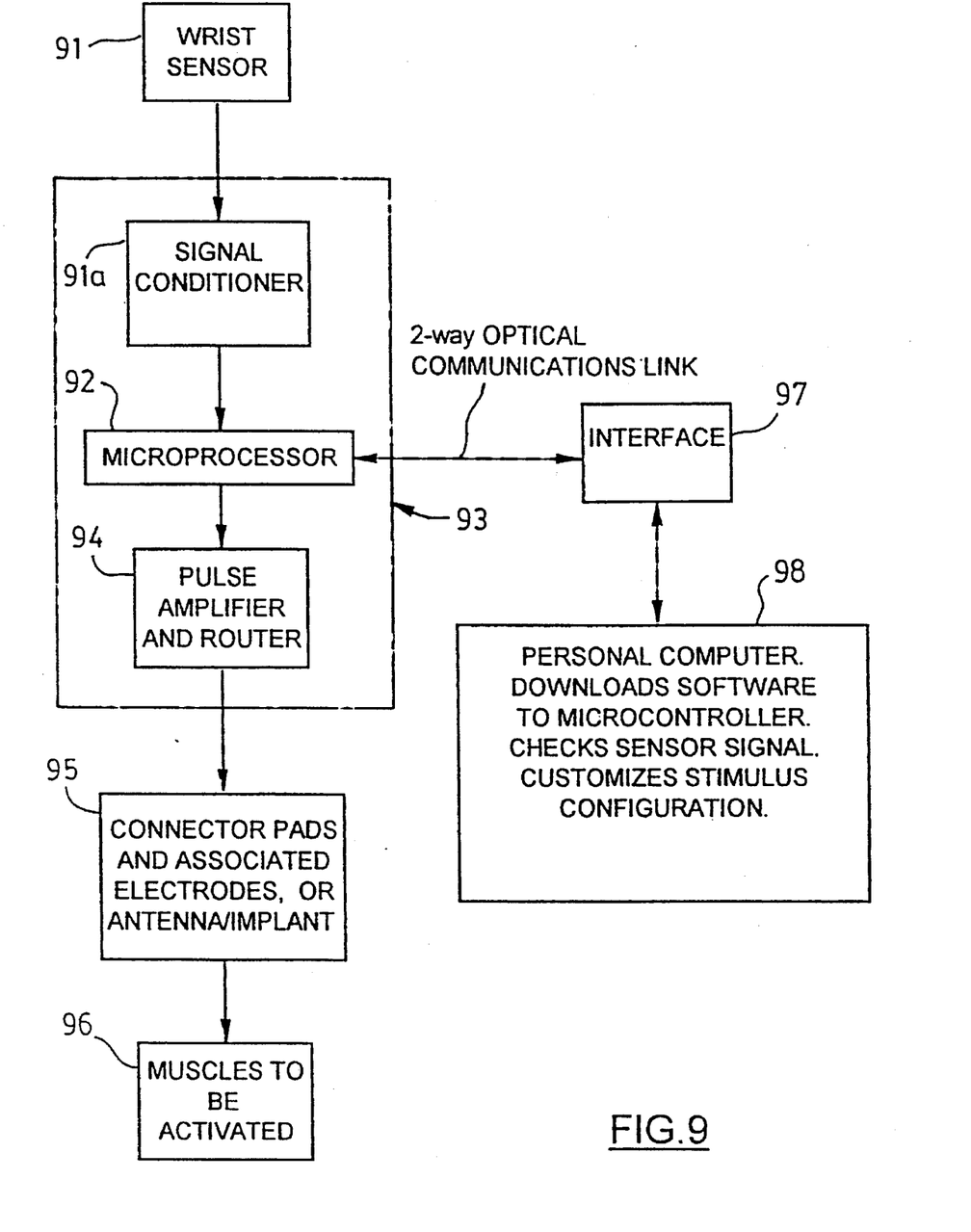
FIG. 9 is a block diagram showing the functional relationships between the elements of the preferred embodiment.

The block diagram of FIG. 9 shows the functional relationship between the components of the system. The sensor block 91 shown in FIG. 9 may comprise the sensor 14 of FIG. 3 or of FIG. 4. Sensor block 91 provides an output signal stimulator controller 93. Stimulator controller 93 consists of signal conditioner 91a for sensor 14, microcontroller 92, and stimulus pulse amplifier and router 94. Microcontroller 92 is preferably a Motorola 68HC11. Microcontroller 92 samples the conditioned sensor signal and on the basis of customized software provides driving signals to stimulus pulse amplifier and router 94. In turn, the stimulus pulse amplifier and router portion of the stimulator controller 93 provides pulse trains to appropriate contact pads and associated electrodes 95, which are preferably of the form illustrated in FIGS. 5 and 6 as electrode 51 and contact pad 52, but may be an antenna and implant system of the types shown in FIG. 7. Interface 97 and computer 98 are for use by a clinician, as discussed below.

A computer may be selectively connected, preferably by an RS232 port, to micro-controller 93 to permit software to be downloaded and stimulus channels and pulse parameters to be configured to suit each patient. Both micro-controller 93 and the computer contain software written to enable the units to carry out the functions described.

Figure 10:
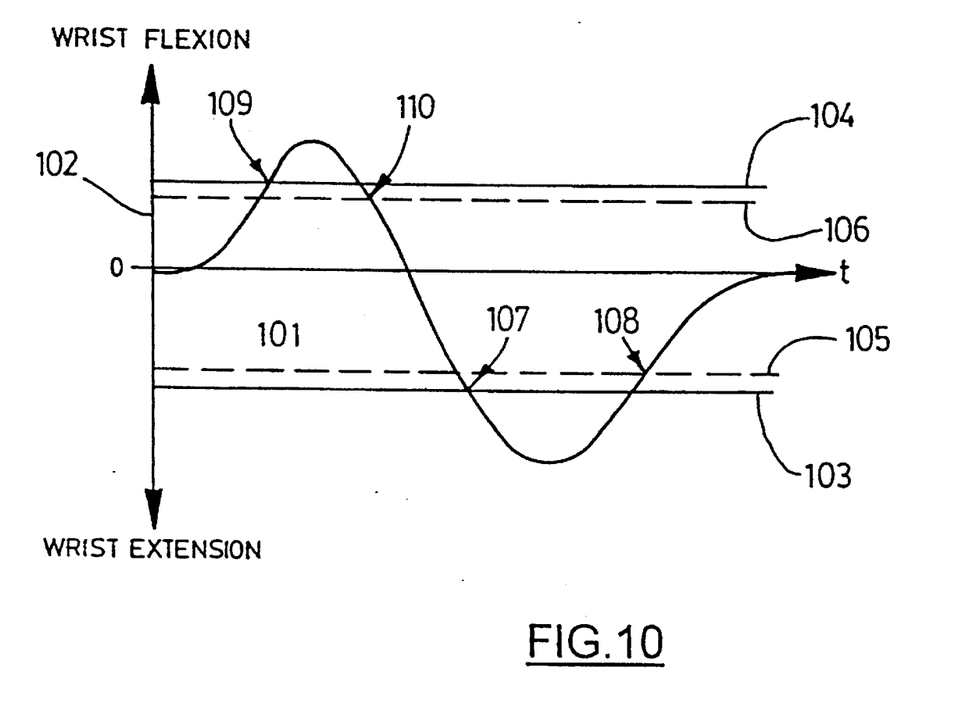
FIG. 10 is a graph showing the stimulus ON and OFF thresholds for the device shown in FIG. 1.

FIG. 10 illustrates a plot of the output of the wrist position sensor of the preferred embodiment on a horizontal axis 101 and a vertical axis 102, showing wrist flexion above the horizontal axis and wrist extension below the horizontal axis. Lines 103 and 104 show the thresholds for turning on pinch-grip FES and hand-opening FES, respectively. The dashed lines 105 and 106 show the thresholds for turning off pinch-grip FES and hand-opening FES stimulation, respectively. The difference (hysteresis) in the ON and OFF thresholds for both pinch grip and hand-opening avoids intermittent ON/OFF switching in cases where the wrist lingers close to the ON threshold. At point 107, the wrist position crosses the threshold for triggering pinch grip FES. At point 108, the wrist position crosses the threshold for turning off pinch grip FES. At point 109, the wrist position crosses the threshold for triggering hand-opening FES. At point 110, the wrist position crosses the threshold for turning off hand-opening FES.

Figure 11:
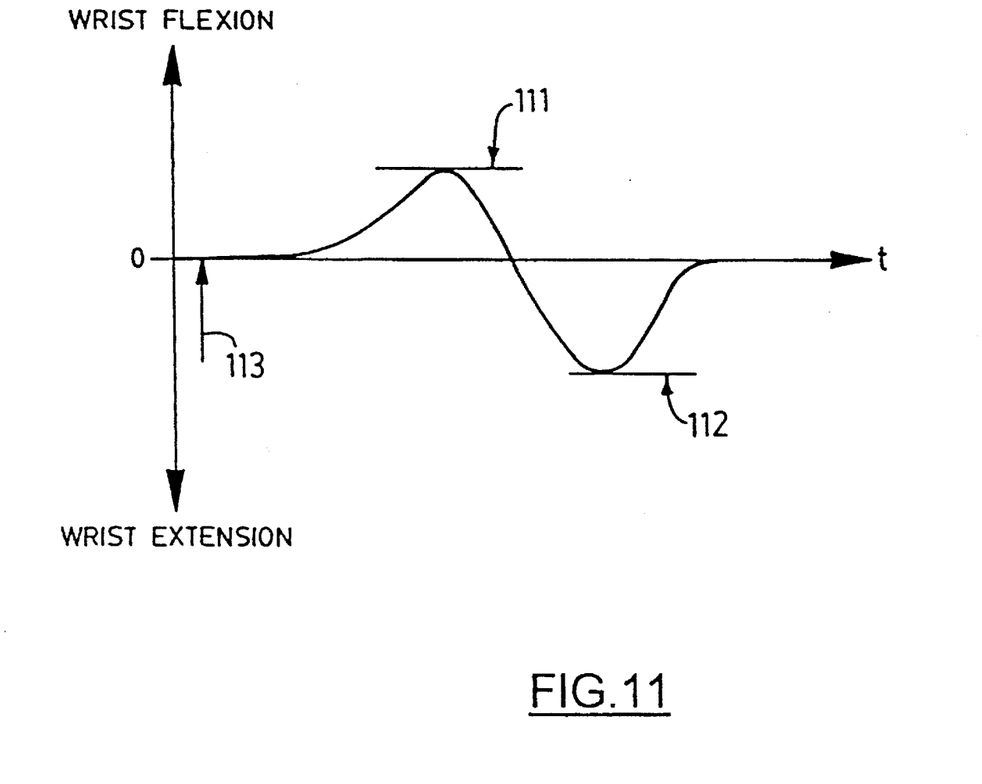
FIG. 11 is a graph showing how the stimulus ON and OFF thresholds for the device shown in FIG. 1 are set.

FIG. 11 illustrates in a graphical manner the way in which the user resets threshold and stimulus intensity parameters. The thresholds are re-set to allow for hand opening or pinch-grip closing with varying degrees of wrist flexion or wrist extension. The user first places the microcontroller 93 shown in FIG. 9 in re-set mode. In the preferred embodiment, this is done by pressing the OPTION button 24 on the upper surface of box 15 of FIG. 1 once. LED 25 of FIG. 2 next to the OPTION button starts blinking and after a second or so if the button has not been pressed again, the diode lights continuously for two-three more seconds during which time the processor is ready to receive the new threshold settings. During this 2–3 seconds, the user moves his/her wrist between the desired threshold positions. The microcontroller 93 of FIG. 9 records the points of greatest wrist flexion and greatest wrist extension caused by tangents 111 and 112, respectively in FIG. 11. The point of greatest wrist flexion selected during the reset procedure is used by microcontroller 93 as the threshold for hand opening FES. Similarly, the tangent 112 representing maximal wrist extension in FIG. 11 is stored by the microcontroller as the threshold for pinch grip FES. The amount of hysterisis referred to above is previously set by the clinician using the computer interface 97 and 98 shown in FIG. 9. The amount of hysterisis is expressed as a percentage of the displacement between tangent 111 and 112 in FIG. 11. When the reset procedure is complete, LED 25 of FIG. 2 goes dark.

Subsequently when the patient flexes the wrist to a position greater than that shown as tangent 111 in FIG. 11, micro-controller 93 of FIG. 9 will cause the stimulus pulse generator 94 to send electrical pulses to those electrodes which are appropriate to cause hand opening. Preferably these stimulate the extensor digitorum and abductor pollicis muscles. Similarly, extension of the wrist by the patient such that the sensor provides a signal corresponding to wrist extension greater than that of tangent 112 of FIG. 11, micro-controller 93 of FIG. 9 will cause the pulse generator 94 to provide a pulse train to those electrodes which are positioned on the patient's hand and foream to produce thumb opposition and finger flexion by stimulating muscles, including flexor pollicis brevis and longus, opponens pollicis and flexor digitorum superficialis muscles, to produce a pinch grip.

Using the OPTION button, the patient can also pre-set the intensity of the stimulus pulse train to each active electrode. The patient selects an electrode by pushing the OPTION button 2, 3 or 4 times in succession. Two pushes selects the flexor pollicis longus electrode, three pushes selects extensor digitorum and so on. The electrode selected is indicated by one of three LEDs 25 on box 15 as shown in FIG. 2. Stimulus intensity can now be changed by using wrist movements. For example, if the intensity of stimulation through the thumb electrodes is too high, flexion of the wrist will decrease it. If the intensity is too low, extension of the wrist will increase it. The changes are gradual and the rate of change can be preset by the clinician using computer interface 97 and 98 shown in FIG. 9. The changes are indicated to the user by visual and/or auditory feedback. Thus, the longer the wrist is kept in flexion, the greater the decrease in intensity of stimulation of the electrodes selected. When a satisfactory intensity is achieved, the OPTION button is pressed to exit from the option mode. It is to be understood that the OPTION button could be replaced by a voice activated input system.

The glove 13 shown in FIGS. 1 and 2 is preferably a form-fitting, elastic glove having an integral sensor of the type shown in FIG. 3, or alternatively FIG. 4. Contact pads of the type shown in FIG. 5 are mounted on the interior surface of glove 13. According to the preferred embodiment of the invention, the microprocessor, pulse generator and the body of the sensor are located in control box 15 which is held in a pouch on the back of the glove itself. The box 15 has the three push-buttons which control power, stimulus ON-OFF and option selection. The micro-controller, pulse generator and body of the sensor are not shown.

In operation, the glove is worn by a user over the hand and forearm as shown in FIG. 1. When the user flexes the wrist, sensor 14 responds to the motion. The sensor signal is sampled digitally by the micro-controller 93. If the position signal exceeds the pre-set hand open threshold, microcontroller 93 provides a pulse train via the stimulus pulse generator to selected electrode contact pads in the glove 13 as shown in the block diagram of FIG. 9 as block 95. The selected connector pad transmits pulses through the skin electrodes to the muscles on the back of the forearm which open the hand as shown in FIG. 1.

Alternatively, the patient may extend the wrist. If wrist extension exceeds the pre-set "pinch grip" threshold, pulses will be transmitted by the electrodes which create a pinch grip as shown in FIG. 2.

In another aspect of the invention, a plurality of pairs of thresholds could be pre-stored by the patient in microcontroller 93. A desired pair of threshold points could subsequently be selected using the option button on box 25.

Figure 12:
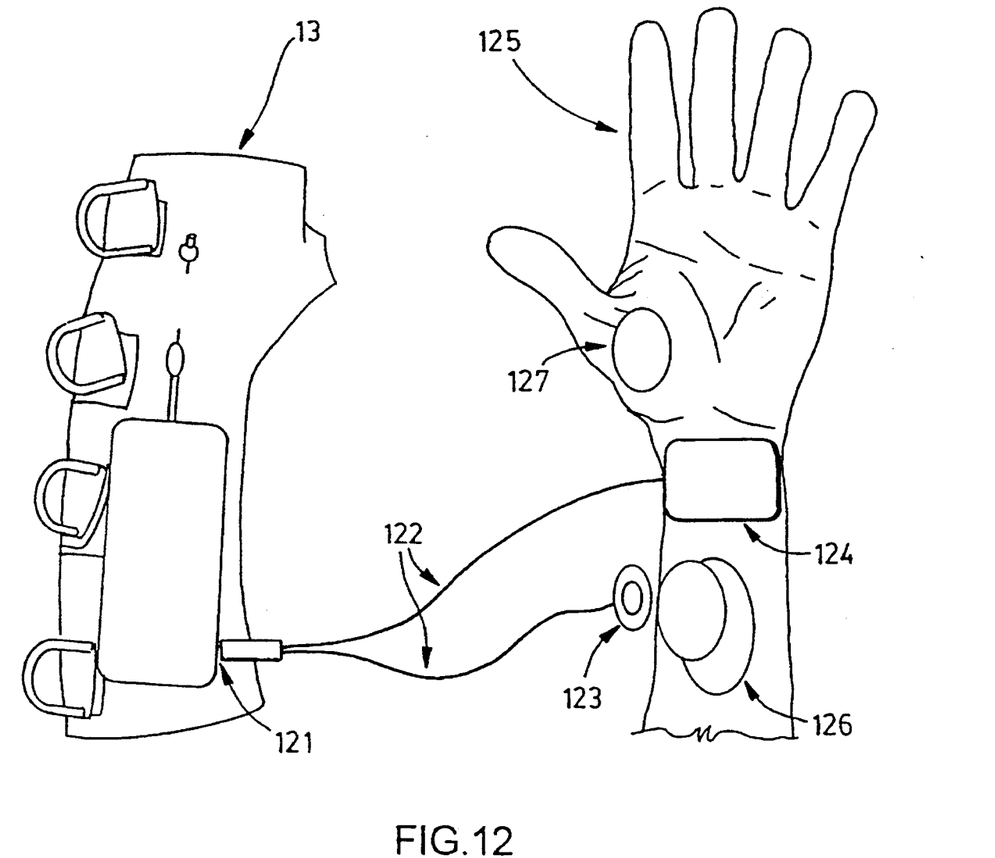
FIG. 12 illustrates how external test leads are connected to a control box to enable exploratory stimulation to determine the position on the skin of "motor points" i.e. best sites for stimulating given muscles.

With respect to FIG. 12, in order to use the preferred embodiment of the glove, electrodes of the type shown as 51 in FIG. 5 and FIG. 6 must be positioned appropriately and accurately on the patient's hand and forearm over "motor points" i.e. at those places which will best give rise to stimulation of the muscles referred to above. The motor points have to be established empirically by the clinician during an initial fitting procedure. A conventional FES stimulator could be used to identify the motor points. However to facilitate the procedure, the preferred embodiment of glove 13 allows external access to the output of micro-controller 93. Test leads 112 are connected to micro-controller box 121 by the clinician. These test leads can then be connected to moist pad electrode 123 and self-adhesive electrode 124 suitable for rapid exploratory stimulation of likely motor points on the patients hand 125. Typical regions of the skin which are explored are indicated on FIG. 12 as 126 and 127 e.g. thumb flexion motor point, index finger flexion motor point and thumb adduction motor point. Electrode 124 is anodic i.e. positive indifferent electrode.

In another aspect of the invention, muscle stimulation is used to attenuate pathological tremor. In this case, the microcontroller is programmed to digitally filter the sampled displacement signal and accordingly stimulate muscles out-of-phase with each tremor cycle. In the preferred embodiment of a tremor control glove, all aspect of the design and use of the glove are as described herein, except for the control algorittun used by the microprocessor. In a further aspect of the invention, it is also believed that the garment or glove provides a more convenient means of applying therapeutic muscle stimulation than existing devices.

It is to be understood that appropriate computer programming is required to conduct the functions discussed above, as will be appreciated by persons skilled in the art.

Controller box 15 and sensor 14 are detachable from the glove. This permits the glove to be washed. All other metallic components of the glove e.g. metal mesh and connecting wires should be resistant to corrosion. A preferred material is stainless steel.

We claim:

1. An electrical stimulation garment for use by a user having muscles of reduced motor ability comprising:

said garment being a non-invasive self-contained functional electrical stimulation garment which may be donned in one piece by said user, said garment being adapted to fit over a joint and said muscles of said user;

said garment including an electronic controller-stimulator for stimulating said muscles of said user;

said garment including a sensor to sense movement of said joint and which is cooperatively interconnected with said electronic controller-stimulator, said electronic controller-stimulator converting sensed movement of said joint into a control signal for functional electrical stimulation of said muscles; and said garment being adapted, when the garment is worn by said user, to pass said functional electrical stimulation from said stimulator through electrical contacts internal to said garment to self-adhesive skin electrodes pre-positioned on said user, to stimulate said muscles of reduced motor ability.

2. The garment of claim 1 in which the electrical contact by the electrical connections is formed upon tightening of the garment on the user.

3. The garment of claim 2 in which the electrical connections are made through a metallic mesh.

4. The garment of claim 2 in which the electrical connections are made through a metallic foil.

5. The garment of claim 2 having a shape in the form of a hand glove.

6. The garment of claim 5 in which the hand glove fits over at least a part of a hand and part of a forearm of the user.

7. The garment of claim 6 in which the joint movement sensor is a wrist movement sensor.

8. The garment of claim 5 in which the joint movement sensor and the controller-stimulator are located on the back of the glove.

9. The garment of claim 8 being capable of being tightened by the user.

10. The garment of claim 9 in which the glove includes Velcro straps and ring-pulls to enable the user of reduced motor ability to don and tighten the garment.

11. The garment of claim 5 in which the controller-stimulator sets threshold limits of flexion and extension of the user's wrist to stimulate opening and closing of the user's hand and further sets an intermediate zone between the threshold limits in which there is no stimulation to open or close.

12. The garment of claim 11 in which the threshold limits are set by the user.

13. The garment of claim 2 in which the electrical contact is by pressure between the said self-adhesive skin electrodes and the internal electrical contacts in the garment.

14. The garment of claim 2 having a shape in the form of a cuff or sleeve.

15. The garment of claim 2 in which the perforated material is elastic perforated material.

16. The garment of claim 1 in which said electrical contacts internal to said garment are adapted to make contact with said self-adhesive skin electrodes, said electrodes having a stud oriented away from the skin of the user.

17. The garment of claim 1 in which the functional electrical stimulation attenuates tremors in the user.

18. The garment of claim 1 in which the reduced motor ability is caused by quadriplegia, paraplegia or hemiplegia.

19. The garment of claim 1 in which the joint movement sensor and the controller-stimulator are detachable from the garment.

20. A non-invasive self-contained functional electrical stimulation hand glove which may be donned in one piece by a user of reduced motor ability, comprising:

said glove being made of an elastic material and being adapted to fit over a wrist on said user;

a wrist movement sensor; and a functional electrical controller-stimulator, said sensor and said controller-stimulator being electrically and cooperatively interconnected.

21. The glove of claim 20 in which the controller-stimulator sets threshold limits of flexion and extension of the user's wrist to stimulate opening and closing of the user's hand and further sets an intermediate zone between the threshold limits in which there is no stimulation to open or close.

22. The glove of claim 21 in which the thresholds of movement may be set to new threshold positions by the user through activation of the controller-stimulator and movement of the wrist between the new threshold positions.

23. The glove of claim 21 in which the controller-stimulator further includes an electrically-isolated communications interface to allow adjustment and review of (a) threshold positions for activation of stimulations for hand opening or closing, (b) stimulus parameters, and (c) control logic.

24. The glove of claim 20 having metallic mesh internal to said glove, said metallic mesh making electrical contact with pre-positioned self-adhesive skin electrodes when the glove is tightened.

25. The glove of claim 20 in which there is an alternative connection to the stimulator output stage to provide a pulse train for precisely locating user's muscle stimulation sites for said opening and closing.

26. A non-invasive self-contained functional electrical stimulation hand glove which may be donned in one piece by a user of reduced motor ability, comprising:

a wrist movement sensor;

a functional electrical controller-stimulator;

opening and closing with the hand being controlled by the controller-stimulator by movement of the wrist beyond threshold limits of flexion and extension thereof, with an intermediate zone between such threshold limits in which there is no stimulation to open or close.

27. A non-invasive self-contained functional electrical stimulation garment which may be donned in one piece by a user of reduced motor ability, comprising in combination:

said garment being made of an elastic material and being adapted to fit over a joint on said user;

metallic mesh patches internal to said garment adapted to make electrical contact with self-adhesive skin electrodes adapted to be on said user when garment is tightened by the user;

said self-adhesive skin electrodes including a stud oriented away from the skin of the user, said stud connecting to the metal mesh by a contact pressure.

28. A method of effecting muscle stimulation of a user of reduced motor ability, comprising:

determining selected muscle stimulation sites on the user;

applying self-adhesive skin electrodes at the sites; and applying a garment, wherein the garment is made of a perforated material and is adapted to fit over a part of the user's body and wherein the garment has electrically and cooperatively interconnected components comprising electrical connections adapted to make contact with the self-adhesive skin electrodes, a joint movement sensor, and a controller-stimulator, for effecting muscle stimulation.

29. The method of claim 28 in which functional electrical stimulation is effected through pre-positioned self-adhesive skin electrodes located on said user at selected muscle stimulation sites.

* * * * *